United States Patent [19]

Asmussen et al.

[11] Patent Number: 5,183,832
[45] Date of Patent: Feb. 2, 1993

[54] COATING AGENT FOR COLLAGEN-CONTAINING MATERIALS

[75] Inventors: Erik Asmussen, Farum; Erik C. Munksgaard, Kokkedal, both of Denmark; Michael Müller, Bergisch Gladbach, Fed. Rep. of Germany; Wolfgang Podszun, Cologne, Fed. Rep. of Germany; Jens Winkel, Cologne-Pesch, Fed. Rep. of Germany

[73] Assignee: Bayer Aktiengesellschaft, Leverkusen, Fed. Rep. of Germany

[21] Appl. No.: 779,115

[22] Filed: Oct. 15, 1991

Related U.S. Application Data

[63] Continuation of Ser. No. 603,594, Oct. 25, 1990, abandoned, and a continuation of Ser. No. 389,847, Aug. 4, 1989, abandoned.

[30] Foreign Application Priority Data

Aug. 19, 1988 [DE] Fed. Rep. of Germany ....... 3828170

[51] Int. Cl.$^5$ ............... C08F 2/50; C08K 5/07; C08G 2/26
[52] U.S. Cl. .................... 522/84; 522/85; 522/103; 523/116
[58] Field of Search ............... 522/84, 85, 103

[56] References Cited

U.S. PATENT DOCUMENTS

| | | | |
|---|---|---|---|
| 4,373,035 | 2/1983 | Bowen | 523/113 |
| 4,459,193 | 7/1984 | Ratcliffe et al. | 523/116 |

FOREIGN PATENT DOCUMENTS

| | | |
|---|---|---|
| 0141324 | 5/1985 | European Pat. Off. |
| 0150952 | 8/1985 | European Pat. Off. |
| 0321683 | 6/1989 | European Pat. Off. |
| WO8201128 | 4/1982 | PCT Int'l Appl. |

OTHER PUBLICATIONS

Patent Abstracts of Japan, vol. 12, No. 96 (C-484) [2943], Mar. 29, 1988, & JP-A-62 230 709 (Mitsui Petrochem. Ind.) Sep. 10, 1987.

*Primary Examiner*—Marion E. McCamish
*Assistant Examiner*—Susan Berman
*Attorney, Agent, or Firm*—Sprung Horn Kramer & Woods

[57] ABSTRACT

Coating agent for collagen-containing materials, comprising an aldehyde, unsaturated monomers with and without active hydrogen, solubilizers and/or dispersants, activators and conventional additives.

2 Claims, No Drawings

COATING AGENT FOR COLLAGEN-CONTAINING MATERIALS

This application is a continuation of application Ser. No. 07/603,594 filed Oct. 25, 1990, and of application Ser. No. 07/389,847 filed Aug. 4, 1989, both abandoned.

The invention relates to formulations which can be used as a coating material, for example as a priming material (primer or liner) or coating, in order to improve a bond between collagen-containing materials and curing polymeric materials.

Collagen-containing materials are scleroprotein substances and main constituents of the human and animal intercellular supporting substances such as cartilage tissue and bone tissue, skin and ebur dentis (dentin). Within the scope of the present invention, the coating agents are preferably used for the treatment of dentin in connection with tooth repairs.

Especially in the dental field, curing polymeric materials are used as filling materials in tooth repairs. Acrylate-based fillings are in general preferred as the curing polymeric materials. These polymeric fillings have, however, the disadvantage of poor adhesion to the dentin. For solving this problem, undercuts on the dentin have hitherto been made in some cases; for this purpose, it was necessary to remove considerable quantities of fresh dentin, beyond the attacked area.

According to another method, the dentin and the surface of the enamel are superficially etched with acids such as, for example, phosphoric acid, and the filling is then carried out. Apart from the fact that the acids exert an irritant action in the buccal region, they also easily penetrate through the dentin canals into the tooth and damage the nerve (pulpa). Moreover, bonding of the filling to the dentin is slight in this method.

From U.S. Pat. No. 4,593,054, coating agents for collagen-containing materials are known, which contain an aldehyde, an olefinically unsaturated monomer having active hydrogen, optionally also as a mixture with an unsaturated monomer having no active hydrogen, water, solvents such as acetone or ethanol, and conventional additives (page 7, lines 24-29, page 10, lines 1-4, and page 14, lines 20-22 of German language equivalent EP-A-141,324).

It has proved to be advantageous, for example in the case of fillings of tooth cavities, first to carry out a conditioning of the fresh dentin surface. Conditioning fluids have in general a pH value from 0.1 to 3.5 and can be an acid having a $pK_s$ value of less than 5 and, optionally, an amphoteric amino compound having a $pK_s$ value in the range from 9.0 to 10.6 and a $pK_B$ value in the range from 11.5 to 12.5.

The coating agents are intended to effect a firm bond, without leaving a gap, between the conditioned dentin surface and the filling material.

A coating material for collagen-containing materials has been found, which contains a) 1-10% by weight of an aldehyde,
b) 10-40% by weight of a water-soluble monomer having active hydrogen,
c) 1-50% by weight of a water-insoluble monomer having two or more polymerizable double bonds,
d) 0.01-2.5% by weight of a photoinitiator,
e) 15-70% by weight of water,
f) 0.2-10% by weight of solubilizers and/or dispersants and
g) 0-5% by weight of additives known per se, the total of the constituents giving 100% by weight.

The coating agent according to the invention effects a firm bond between the conditioned dentin surface and the filling material; in this way, the tooth repair will last for many years.

The aldehydes (a) can be aliphatic, aromatic or heterocyclic aldehydes.

In aliphatic monoaldehydes and dialdehydes, the aldehyde functional group is bound to an aliphatic, straight-chain or branched hydrocarbon radical having 1 to 20, preferably 2 to 10 and especially preferably 2 to 6 carbon atoms. As the aliphatic radicals, methyl, ethyl, propyl, isopropyl, butyl, isobutyl, pentyl, isopentyl, hexyl, isohexyl and hydroxyethyl may be mentioned by way of example. Examples of aliphatic aldehydes are formaldehyde, acetaldehyde, butyraldehyde, glutaric dialdehyde and glyoxal.

In aromatic aldehydes, the aldehyde functional group is bound to an aromatic radical. As the aromatic radicals, aromatic hydrocarbons having 6 to 12 carbon atoms, preferably phenyl, naphthyl and biphenyl may be mentioned. The aromatic radicals can be substituted, for example, by alkyl ($C_1$ to $C_6$), alkoxy ($C_1$ to $C_6$), hydroxyl or carboxyl.

As examples of aromatic aldehydes may be mentioned: benzaldehyde, salicylaldehyde, vanillin and phthalaldehyde.

In heterocyclic aldehydes, the aldehyde functional group is bound to the heterocyclic ring. Furfural may be mentioned as an example.

The aldehydes for the coating agents according to the invention can be monoaldehydes or dialdehydes.

Aliphatic monoaldehydes and dialdehydes are preferred for the coating agents according to the invention.

Water-soluble monomers are to be understood as unsaturated monomers which have a water-solubility at 20° C. of more than 5% by weight, preferably 10 to 100% by weight, relative to the mixture of monomer and water.

Acrylic acid and methacrylic acid and derivatives thereof, such as the acid amides and hydroxyalkyl ($C_2$ to $C_6$) esters, are preferred.

(Meth)acrylic acid, methacrylamide, hydroxyalkyl ($C_2$ to $C_5$) methacrylates such as hydroxyethyl methacrylate and hydroxypropyl methacrylate, as well as the ethylene, diethylene and triethylene glycol monomethacrylates may be mentioned as examples.

The water-insoluble, unsaturated monomers have a water-solubility at 20° C. of less than 5% by weight, preferably 0.01 to 3% by weight. They contain two or more polymerizable double bonds in the molecule, methacrylic and acrylic acid esters of 2-hydric to 5-hydric alcohols having 2 to 30 carbon atoms being particularly suitable. Alkoxy-(meth)acrylates and (meth)acrylate containing urethane groups are particularly preferred.

(Meth)acrylic acid esters of the formula

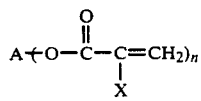

in which

A denotes an n-valent, straight-chain, branched, cyclic, aliphatic, aromatic or mixed aliphatic/aromatic radical having 2 to 25 carbon atoms,
which can also be interrupted by —O— or NH—bridges and can be substituted by hydroxy, oxy, carboxy, amino or halogen, X denotes H or methyl and
n represents an integer from 2 to 8, preferably 2 to 4, may be mentioned as examples.

Compounds of the following formulae may be mentioned as preferred:

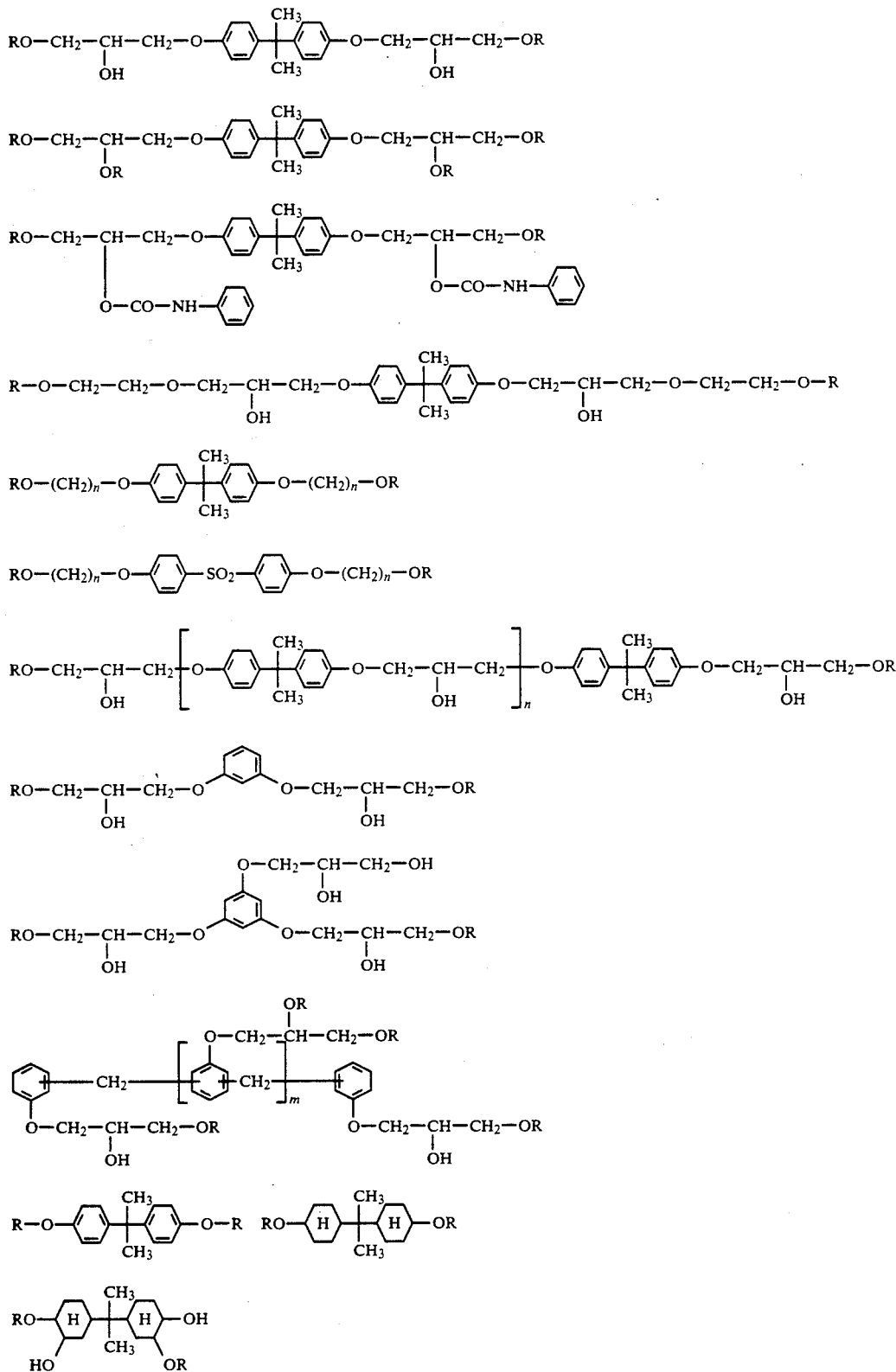

-continued
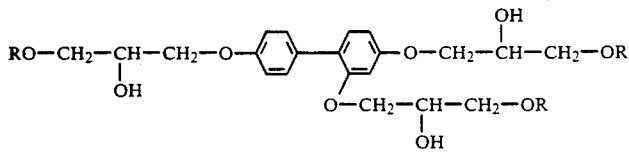
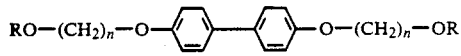
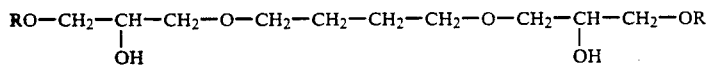
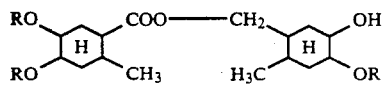
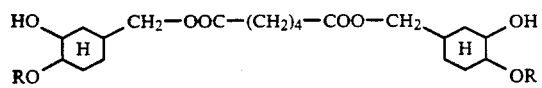
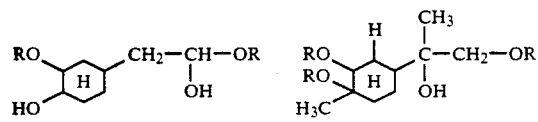
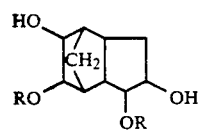
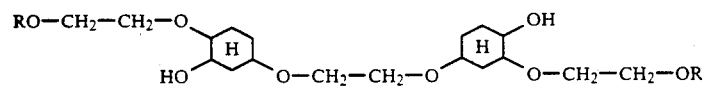
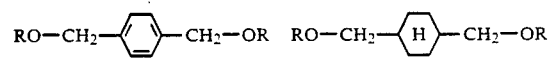
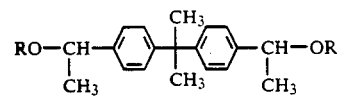
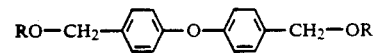
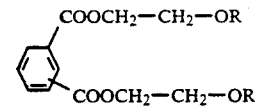
in the ortho, meta or para form
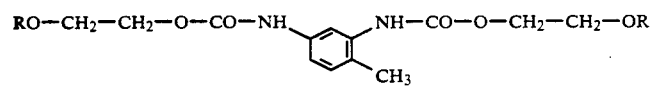
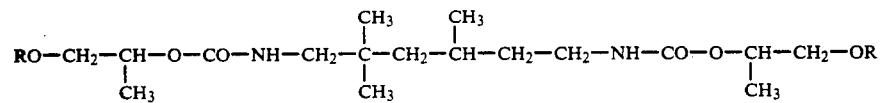
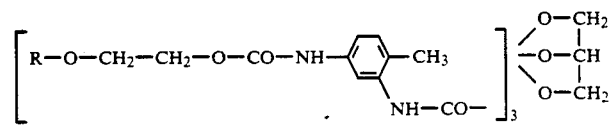

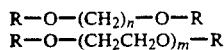

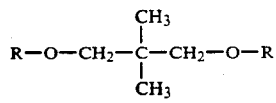

wherein
R represents

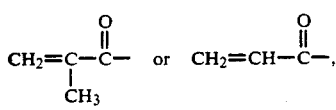

n denotes a number from 1 to 4 and
m denotes a number from 0 to 5.

In addition, the derivatives of tricyclodecane (U.S. Pat. No. 4,323,696) and reaction products of polyols, diisocyanates and hydroxyalkyl methacrylates (U.S. Pat. No. 4,952,614, U.S. Pat. No. 5,439,770 and U.S. Pat. No. 4,879,402) should be mentioned.

A particularly preferred monomer is the so-called bis-GMA of the formula

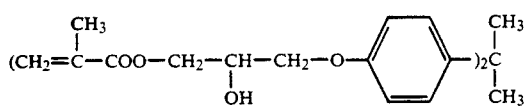

It is of course possible to employ mixtures of the various (meth)acrylic acid esters which can form crosslinks. Mixtures of 20 to 70 parts by weight of bis-GMA and 30 to 80 parts by weight of triethylene glycol dimethacrylate may be mentioned by way of example.

Photoinitiators (d) are known per se (Houben-Weyl, Methoden der organischen Chemie [Methods of Organic Chemistry], volume E20, pages 80 et seq., Georg Thieme Verlag Stuttgart, 1987). Preferably, these are carbonyl compounds, such as benzoin and derivatives thereof, in particular benzoin methyl ether, benzil and benzil derivatives, for example 4,4-oxydibenzil, and other dicarbonyl compounds such as diacetyl, 2,3-pentanedione and α-diketo derivatives of norbornane and substituted norbornanes such as camphorquinone, metal carbonyls such as pentacarbonyl manganese, quinones such as 9,10-phenanthrenequinone and naphthoquinone The coating materials according to the invention preferably also contain co-activators which accelerate the polymerization reaction in the presence of photopolymerization initiators. Examples of known accelerators are aromatic amines such as p-toluidine and dimethyl-p-toluidine, trialkylamines such as trihexylamine, polyamines such as N,N,N′,N′-tetraalkylalkylenediamines, barbituric acid and dialkylbarbituric acid.

The accelerators are in general contained in the coating material in a quantity from 0.01 to about 5% by weight. Alkylaminoarylsulphonamides of the formula

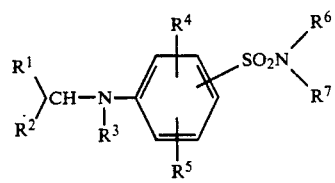

wherein
$R^1$ and $R^2$ are identical or different and denote hydrogen, methyl, vinyl or phenyl,
$R^3$ denotes hydrogen, methyl and ethyl,
$R^4$ and $R^5$ are identical or different and denote hydrogen, halogen or methyl, or $R^4$ and $R^5$ in ortho-positions can be parts of a fused aromatic six-membered ring,
$R^6$ and $R^7$ are identical or different and denote hydrogen, methyl, allyl, methallyl, cyclohexyl, phenyl, benzyl, hydroxyethyl, hydroxypropyl, acryloyloxyalkyl, methacryloyloxyalkyl, 2,3-epoxypropyl or 1,2-dihydroxyprop-1-yl (meth)acrylate, it being possible for $R^6$ and $R^7$ to be linked to form a morpholine or piperidine radical,
may also be mentioned as co-activators.

The following may be mentioned as examples of alkylaminoarylsulphonamides:
N,N-Dimethyl-p-dimethylaminobenzenesulphonic acid amide and N-hydroxyethyl-p-dimethylaminobenzenesulphonic acid amide.

The water (e) can, for example, be demineralized water.

Solubilizers within the scope of the present invention are volatile solvents (vapour pressure at 25° C. more than 1000 Pa) from the group comprising the ketones, alcohols and ethers. Aliphatic ketones having 3 to 6 carbon atoms, aliphatic alcohols having 1 to 5 carbon atoms, glycol monoalkyl($C_1$ to $C_4$) ethers and cyclic ethers ($C_4$ to $C_6$) are preferred. The following may be mentioned as examples: acetone, butanone, methanol, ethanol, propanol, isopropanol, butanol, isobutanol, sec.-butanol, tert.-butanol, ethylene glycol monomethyl ether, tetrahydrofuran and 1,4-dioxane.

The dispersants (f) which can be used according to the invention can be ionic and nonionic surfactants.

Examples of preferred anionic surfactants are: phosphates such as the sodium salt of di-2-ethylhexyl phosphate, alcohol sulphates such as oleyl alcohol sulphate, alkyl ($C_6$ to $C_{20}$)benzenesulphonates and alkyl($C_8$ to $C_{24}$)sulphonates, in particular the Na salt of sulphosuccinic acid dioctyl ester.

Preferred cationic surfactants can, for example, be: quaternary ammonium salts such as, for example, methyltrioctylammonium chloride and methyltricaprylylammonium chloride.

Nonionic surfactants in the form of fatty acid derivatives of polyols or ethylene oxide, ethoxylated fatty alcohols and phenols as well as amphoteric surfactants such as alkylaminoethanesulphonic acid can also be used according to the invention. Surface-active, high-molecular compounds are particularly preferred. Water-soluble polyvinyl compounds such as polyvinyl acetate, polymethacrylic acid and polyacrylic acid as well as alkali metal salts thereof, copolymers of sodium methacrylate and methacrylic acid alkyl esters may be mentioned here. Cellulose derivatives such as methylcellulose and carboxymethylcellulose are also very suitable. Poly-N-vinyl-2-pyrrolidone is very particularly suitable.

The additives known per se can be stabilizers, inhibitors, light stabilizers, dyestuffs, pigments and fluorescent substances.

Those coating agents for collagen-containing materials are preferred which contain
a) 2 to 8% by weight of an aldehyde,
b) 15 to 40% by weight of a water-soluble monomer having active hydrogen,
c) 2 to 40% by weight of a water-insoluble monomer having two or more polymerizable double bonds,
d) 0.01 to 2.5% by weight of a photoinitiator,
e) 25 to 60% by weight of water,
f) 0.5 to 10% by weight of solubilizers and/or dispersants and
g) 0 to 5% by weight of additives known per se, the total of the constituents giving 100% by weight.

Before a collagen-containing material is coated with the coating material according to the invention, the former is in general treated with a conditioning fluid. The composition of the conditioning fluid depends on the type of the material to be coated. For tooth enamel, 15–60% strength aqueous solutions of ortho-phosphoric acid are particularly suitable. As conditioning solutions for ebur dentis (dentin), it is possible to use, for example, aqueous solutions of EDTA (for example 0.5 molar, adjusted to pH 7.4 with NaOH) or aqueous solutions which contain 10% of citric acid and 3% of iron(III) chloride.

Conditioning fluids for a wide field of use, which can be employed especially for tooth enamel and dentin, contain acids having a $pK_s$ value of less than 5 and optionally an amphoteric amino compound having a $pK_s$ value in the range from 9.0 to 10.6 and a $pK_B$ value in the range from 11.5 to 12.5. The conditioning fluids can contain the following acids: phosphoric acid, nitric acid, pyruvic acid, citric acid, oxalic acid, ethylenediaminetetraacetic acid, acetic acid, tartaric acid, malic acid and maleic acid.

Amphoteric amino compounds to be mentioned are preferably compounds of the formula

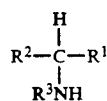

in which
R$^1$ represents a carboxyl group,
R$^2$ denotes hydrogen or a lower alkyl radical which is optionally substituted by hydroxy, thio, methylthio, carboxy, amino, phenyl, hydroxyphenyl or the groups

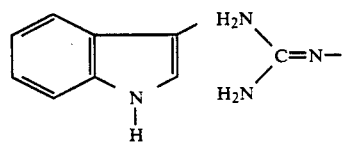

R$^3$ denotes hydrogen or phenyl,
it being possible for the radicals R$^1$ and R$^3$ to be linked by a propyl radical, or in which
R$^1$ represents hydrogen,
R$^2$ denotes the group —A—NH$_3$X, in which
A represents a bidentate alkylene radical having 1 to 6 carbon atoms and
X represents halogen, and
R$^3$ denotes hydrogen.

The following amphoteric amino compounds may be mentioned as examples: glycine, serine, threonine, cysteine, thyrosine, asparagine, glutamine, alanine, valine, leucine, isoleucine, proline, methionine, phenylalanine, tryptophan, lysine, arginine, histidine, N-phenylglycine, ethylenediamine hydrochloride, propylenediamine hydrobromide, butylenediamine hydrochloride, butylenediamine hydrobromide, leucine hydrochloride and histidine hydrochloride.

In addition, the conditioning fluid can also contain substances from the group of the polyethylene glycols and metal hydroxides. In particular, the abovementioned polybasic acids can also be employed as partial metal salts, as long as free acid functional groups remain.

Conditioning fluids which contain at least one of the acids from the group comprising pyruvic acid, ethylenediaminetetraacetic acid and citric acid as well as optionally an amphoteric amino compound from the group comprising glycine, n-phenylglycine and proline, are particularly preferred.

The coating agents according to the invention are in general prepared by mixing the components.

The formulations according to the invention can be used as coating agents, preferably as priming agents (primer or liner) or coating (varnish) for improving the bonding between collagen-containing materials and curing polymeric materials.

Collagen-containing materials occur in many places in the human and animal body. The use according to the invention relates of course to living and non-living materials. Teeth, bones, skin and leather may be mentioned as collagen-containing materials. The formulations according to the invention are preferably used for coating teeth in preparation for tooth fillings during tooth repairs.

The curing polymeric materials are determined essentially by the field of application. Thus, for example, in the dental field, only monomers can be used for the polymerization which are physiologically acceptable and which can polymerize in the buccal region, and bis-GMA (bisphenol-A-diglycidyl dimethacrylate) may be mentioned as an example.

In use, for example in a tooth repair, the conditioning fluid described is first applied, after mechanical cleaning of the collagen-containing tooth material, by means of a little cottonwool and is allowed to act for 60 seconds, and the tooth material is rinsed with water and dried in an air stream. The coating material according to the invention is then applied in a thin layer by means of a small brush, and excess material is spread in an air stream. The tooth filling compound is then applied to the coating material and cured together with the latter.

EXAMPLES 1 TO 5

Coating Materials According to the Invention

Mixtures having the compositions listed below are prepared by means of a high-speed stirrer (2000 revolutions per minute).

EXAMPLE 1

5 g of glutaric dialdehyde
33 g of 2-hydroxyethyl methacrylate
2 g of bis-GMA
0.1 g of camphorquinone (photoinitiator)
55 g of water
5 g of acetone

EXAMPLE 2

5 g of glutaric dialdehyde
33 g of 2-hydroxyethyl methacrylate
2 g of bis-GMA
0.1 g of camphorquinone
59.2 g of water
0.7 g of poly-N-vinyl-2-pyrrolidone

EXAMPLE 3

3.3 g of glutaric dialdehyde
23.4 g of 2-hydroxyethyl methacrylate
12.6 g of triethylene glycol dimethacrylate
20.5 g of bis-GMA
67 mg of camphorquinone
167 mg of N,N-dimethylaminobenzenesulphonic acid diallylamide (co-activator)
38.1 g of water
2 g of poly-N-vinyl-2-pyrrolidone
33 mg of 2,6-di-tert.-butyl-4-methylphenol (stabilizer)

EXAMPLE 4

3.3 g of glutaric dialdehyde
23.4 g of 2-hydroxyethyl methacrylate
20.8 g of bis-GMA
12.7 g of triethylene glycol dimethacrylate
70 mg of camphorquinone
39.3 g of water
0.5 g of methyl-tricaprylammonium chloride

EXAMPLE 5

2.5 g of glutaric dialdehyde
18 g of 2-hydroxyethyl methacrylate
30 g of bis-GMA
17.5 g of triethylene glycol dimethacrylate
100 mg of camphorquinone
29.5 g of water
2.5 g of poly-N-vinyl-2-pyrrolidone

EXAMPLE 6

Application Test

The suitability of the coating materials of Examples 1 to 5 is tested by determining the bonding strength of a plastic material, which contains bis-GMA and triethylene glycol dimethacrylate as the monomers and camphorquinone as the photoinitiator, to dentin and enamel, which have been pretreated with a conditioning fluid (60 seconds time of action, rinsing with water, drying with air) and the coating material (60 seconds time of action, drying with air).

Human teeth which have been extracted and stored in the moist state are used for the test. The teeth are embedded in an epoxide resin by casting. For the measurement on dentin, a smooth dentin surface is produced by wet polishing. Final polishing is carried out with carbon paper 1000.

To prepare a test specimen for measuring the bonding strength, a cylindrical split Teflon mould is clamped to the dentin surface which has been treated as described above (Scand. J. Dent. Res. 88, 348-351 (1980)). The photocuring plastic filling material is filled in as the filling compound. A No. 016 round drill clamped into a hole in a drill holder is fixed to the Teflon mould and pressed from above into the layer of material which is still undergoing the curing process.

The entire arrangement is left to stand undisturbed for 10 minutes at room temperature ($23\pm2°$ C.), whereupon the drill holder and the Teflon mould are taken off and the sample is put down under water at a temperature of $23\pm1°$ C. After 24 hours, the sample is mounted by means of the drill in an Instron tensile test apparatus (Scand. J. Dent. Res. 88, 348-351 (1980)); a tensile strength measurement is carried out at a speed of 1 mm/minute. The tensile strength is calculated by dividing the load, applied at fracture of the filling, by the cross-sectional area in the fracture surface of the test specimen. 5 measurements were carried out in each case on test specimens. The following solutions were used here as the conditioning fluids:

K 1:
    9.1% of pyruvic acid
    9.1% of glycine
    81.8% of water

K 2:
    17% of disodium ethylenediaminetetraacetate dihydrate
    1.7% of sodium hydroxide
    81.3% of water K 3:
    35% of ortho-phosphoric acid
    65% of water.

The results of the bonding strength measurements are summarized in the table which follows:

| Coating material | Dentin | | Enamel | |
|---|---|---|---|---|
| | Conditioning fluid | Bonding strength [N/mm$^2$] | Conditioning fluid | Bonding strength [N/mm$^2$] |
| Example 1 | K 1 | 15 ± 4 | K 1 | 14.8 ± 0.5 |
| Example 2 | K 1 | 19 ± 2 | K 1 | 16.2 ± 3.7 |
| Example 2 | K 2 | 12.3 ± 1 | | |
| Example 3 | K 2 | 11.8 ± 4 | K 3 | 12.6 ± 3.2 |
| Example 4 | K 2 | 13.5 ± 3 | K 3 | 17.0 ± 2.1 |
| Example 5 | K 2 | 14.1 ± 3 | K 3 | 13.2 ∓ 3.5 |

EXAMPLE 7

Comparison Test

A coating material of the following composition was prepared:
2.5 g of glutaric dialdehyde
18 g of 2-hydroxyethyl methacrylate
30 g of bis-GMA
17.5 g of triethylene glycol dimethacrylate
100 mg of camphorquinone
7.5 g of water
24.5 g of acetone.

The bonding strengths on dentin and enamel were determined according to the procedure described in Example 6.

| Dentin | | Enamel | |
|---|---|---|---|
| Conditioning fluid | Bonding strength [N/mm$^2$] | Conditioning fluid | Bonding strength [N/mm$^2$] |
| K 2 | 1,0 | K 3 | 7.2 |

What is claimed is:

1. A coating agent for collagen-containing materials, comprising the following ingredients:
    a) 2-8% by weight of an aldehyde selected from the group consisting of formaldehyde, acetaldehyde, butyraldehyde, glutaric dialdehyde, glyoxal, benzaldehyde, salicylaldehyde, vanillin, phthalaldehyde, and furfural;
    b) 15-40% by weight of a water-soluble monomer selected from the group consisting of (meth)acrylic acid, methacrylamide, hydroxyethyl methacrylate, hydroxypropyl methacrylate, ethylene glycol monomethacrylate, diethylene glycol monomethacrylate, triethylene glycol monomethacrylate, and triethylene glycol dimethacrylate;
    c) 2-50% by weight bis-GMA;
    d) 0.01-2.5% by weight of photoinitiator;
    e) 25-60% by weight of water; and
    f) 0.5-5% by weight of a constituent selected from the group consisting of acetone, butanone, methanol, ethanol, propanol, isopropanol, butanol, isobutanol, sec.-butanol, tert.-butanol, ethylene glycol monomethyl ether, tetrahydrofuran, 1,4-dioxane, the sodium salt of di-2-ethylhexylphosphate, oleyl alcohol sulphate, the sodium salt of sulphosuccinic acid dioctyl ester, methyltrioctylammonium chloride, methyltricaprylylammonium chloride, and poly-N-vinyl-2-pyrrolidone;

the total of constituents giving 100% by weight.

2. A coating material according to claim 1, wherein ingredient f) is poly-N-vinyl-2-pyrrolidone.

* * * * *